United States Patent
Kuhn

(10) Patent No.: US 7,805,318 B1
(45) Date of Patent: Sep. 28, 2010

(54) USING A NON-PROFIT ORGANIZATION TO SATISFY MEDICARE OUT-OF-POCKET/TROOP AND PRODUCT REPLACEMENT

(75) Inventor: Dana A. Kuhn, Midlothian, VA (US)

(73) Assignee: Patient Services Incorporated, Midlothian, VA (US)

( * ) Notice: Subject to any disclaimer, the term of this patent is extended or adjusted under 35 U.S.C. 154(b) by 184 days.

(21) Appl. No.: 11/939,980

(22) Filed: Nov. 14, 2007

Related U.S. Application Data

(60) Provisional application No. 60/866,382, filed on Nov. 17, 2006.

(51) Int. Cl.
*G06Q 10/00* (2006.01)
*G06Q 40/00* (2006.01)
*G06F 19/00* (2006.01)

(52) U.S. Cl. .................................. 705/2; 705/3; 705/4

(58) Field of Classification Search ................... 705/2–3

See application file for complete search history.

(56) References Cited

U.S. PATENT DOCUMENTS

2005/0071191 A1* 3/2005 Wilson et al. .................. 705/2

OTHER PUBLICATIONS

"CMS Releases Final Regulations on Medicare Drug Benefit, Dual Eligibles to be 'Auto-Enrolled'", www.nami.org, Jan. 28, 2005.*
"HPMS Q & A—Patient Assistance Programs", Centers for Medicare & Medicaid Services, Center for Beneficiary Choices Memorandum, Oct. 4, 2006.*

* cited by examiner

*Primary Examiner*—Robert W Morgan
*Assistant Examiner*—Joseph Burgess
(74) *Attorney, Agent, or Firm*—Townsend and Townsend and Crew LLP

(57) ABSTRACT

A process of providing needy Medicare recipients with financial help in addressing medical care by setting up a non-profit organization, receiving donated pharmaceutical product from pharmaceutical manufacturers to the non-profit organization, inventorying the drug product received from the pharmaceutical manufacturers in a contracted or non-profit pharmacy, and taking title of the drug product from the pharmaceutical manufacturers. The drug product replaces a drug product used by the Medicare recipients and the drug product accounts toward the recipient's true out-of-pocket payment (TrOOP).

18 Claims, 4 Drawing Sheets

Diagram 1: Part D

USING A NON-PROFIT ORGANIZATION TO SATISFY MEDICARE OUT-OF-POCKET/TROOP AND PRODUCT REPLACEMENT

CROSS-REFERENCES TO RELATED APPLICATIONS

This application claims priority under 35 U.S.C. §119(e) to U.S. Provisional Patent Application Ser. No. 60/866,382, filed on Nov. 17, 2006, the contents of which are incorporated herein by reference in its entirety.

BACKGROUND OF THE INVENTION

1. Field of the Invention

The invention is directed to addressing the needs of Medicare beneficiaries who cannot afford the prescription drug costs or treatments, but could by using a non-profit organization and/or non-profit pharmacy that can legally accept pharmaceutical drug donations that may replace hospital based drug products used for Medicare beneficiaries which are not normally covered under Medicare and/or satisfy TrOOP with Medicare Part D beneficiaries.

2. Related Art

Medicare is a health insurance program that covers people who either 65 years in age and over, or those who meet other special criteria. Medicare is a program that is administered by the United States government. Medicare has four basic benefit components. Part A is directed to hospital insurance and covers hospital stays and may pay for nursing home services as well if certain criteria are met. Part B is medical insurance coverage and helps pay for services and products which may not be covered under Part A. Medicare Part C is directed to various Medicare advantage plans where a patient will receive benefits through private health insurance plans. Medicare Part D is directed to prescription drug plans, whereas anyone who is eligible for Part A or Part B is also eligible for the Part D prescription drug plans.

Medicare does not pay for all the covered expenses or medical costs for a medical procedure for a patient under Medicare Parts B, for example only. Medicare requires the payment of premiums, deductibles, and co-pays. Additionally, Medicare under Part B may often not cover every procedure, every product, or the like.

The challenge often faced by Medicare recipients receiving care under Part B, is that often a medical procedure that is needed by the patient may be covered under Medicare Part B however, a drug product may be needed during the procedure that is not covered. Accordingly, some patients cannot afford the medical treatment even though the actual procedure is covered by Medicare because the patient cannot afford the drug product that is required by the procedure. For example, a Medicare patient may need a knee replacement. However, because he is a hemophilic, he also must receive the drug product factor concentrate in order to undergo the medical procedure. Accordingly, because Medicare Part B will cover the knee replacement, but not cover the expensive drug product factor concentrate, the Medicare patient cannot afford the procedure. Often a pharmaceutical manufacturer of drug product factor concentrate may be willing to "replace" the drug product in the hospital so the patient may receive this procedure. However, under Medicare law, such an act by the pharmaceutical manufacturer may be construed as an enticement or an inducement. Accordingly, the pharmaceutical manufacturer cannot legally provide the drug product to the Medicare patient in a hospital setting.

Treatment in the form of receiving prescription drug medications under Part D has a deductible associated with it that can be a financial barrier to needy patients. In this regard, the standard benefit under Part D is defined in terms of a benefit structure. For example, the standard benefit may require a deductible to be paid prior to coverage (such as a $250.00 in 2006). The patient then pays 25% of the cost of the covered prescription medication under Part D up to an initial coverage limit ($2,250.00 in 2006, now $2,400.00 in 2007). Once initial coverage limit has been reached by the patient's payment, the patient may be subject to another deductible referred to as the coverage gap but also referred to as a "doughnut hole." Once the patient reaches the "donut hole," the patient will have to continue to pay the full cost of the medication until the true out-of-pocket expense for the medication for that year including the deductible and co-insurance reaches a particular level ($3,600.00 in 2006, now $3,850.00 in 2007). Thereafter, the Medicare patient reaches catastrophic coverage in which the patient can then receive a reduced cost for generic and other prescription medication requiring only a small coinsurance percentage. The size of this donut hole is expected to increase annually as the overall price of drugs increases.

This donut hole obviously causes many patients financial hardship. Moreover, many patients discontinue therapy even after coverage resumes.

The only out-of-pocket costs that can typically count toward this catastrophic coverage are called true out-of-pocket (TrOOP) expenditures. The only time the patient can count the expenditures toward the TrOOP limitation is when the drugs are purchased in accordance with various government and other restrictions.

With respect to Part D of the Medicare Modernization Act, a common challenge for Medicare recipients is to afford the deductible and co-insurance TrOOP. Pharmaceutical manufacturers are currently petitioning the Office of the Inspector General (OIG) to allow their donated product to count toward meeting a Medicare patient's TrOOP. The OIG has in the past been against drug product donations by pharmaceutical manufacturers counting toward TrOOP, and has confirmed this with its last three rendered opinions in 2006. The OIG has allowed "cash" donations paid to non-profit organizations paying a Medicare patient's co-insurance to count toward satisfying TrOOP. However, the pharmaceutical manufacturers could not legally allow their free drug product donations to count toward TrOOP to benefit Medicare recipients.

Accordingly, there is a need for providing products to Medicare patients receiving Medicare Part B coverage. Moreover there is a need for Medicare patients receiving coverage under Part D to allow them to receive free drug product that will count toward their true out-of-pocket deductible.

BRIEF SUMMARY OF THE INVENTION

The invention meets the foregoing needs and allows a non-profit organization to address the drug products needed by Medicare recipients under Part B, and also to provide drug product that satisfies true out-of-pocket (TrOOP) expenses for recipients of Part D.

Accordingly, in one aspect of the invention, a process of providing needy Medicare recipients with financial help in addressing medical care by setting up a non-profit organization, receiving pharmaceutical product at the non-profit organization from multiple pharmaceutical manufacturers for disease specific conditions, inventorying the product received from the multiple pharmaceutical manufacturers, and taking title of the drug product from the multiple pharmaceutical manufacturers. The drug product is physically accepted by a contracted pharmacy or by the organizations non-profit pharmacy. The drug product then replaces a drug product used by the Medicare recipients and the drug product counts toward the recipient's true out of pocket payment.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention, are incorporated in and constitute a part of this specification, illustrate embodiments of the invention and together with the detailed description serve to explain the principles of the invention. No attempt is made to show structural details of the invention in more detail than may be necessary for a fundamental understanding of the invention and the various ways in which it may be practiced. In the drawings.

DETAILED DESCRIPTION OF THE INVENTION

Figure 1:
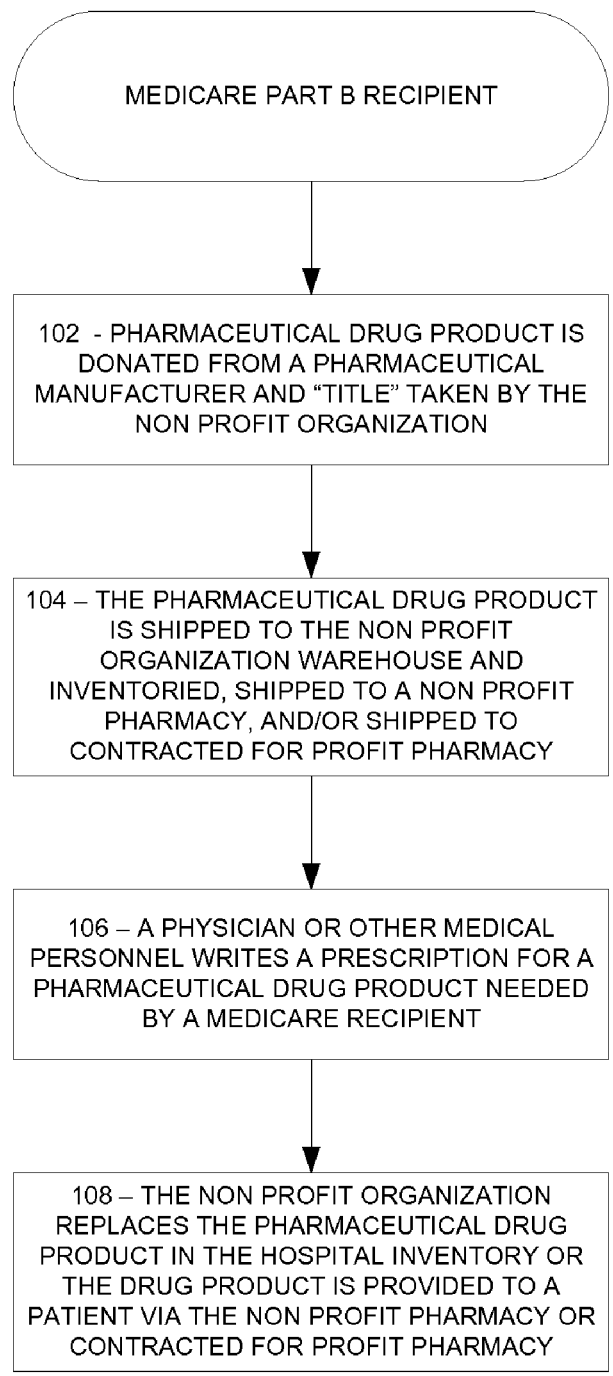
FIG. 1 illustrates a process flowchart for addressing the needs of Medicare Part B recipients according to the principles of the invention.

The embodiments of the invention and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the invention. The examples used herein are intended merely to facilitate an understanding of ways in which the invention may be practiced and to further enable those of skill in the art to practice the embodiments of the invention. Accordingly, the examples and embodiments herein should not be construed as limiting the scope of the invention, which is defined solely by the appended claims and applicable law. Moreover, it is noted that like reference numerals represent similar parts throughout the several views of the drawings.

The invention overcomes the pitfalls of not being able to receive needed product under Part B of the Medicare Act and the inability to receive prescription product donations to address true out-of-pocket expenses (TrOOP). In particular, the invention addresses the need by developing and implementing a "bona fide" non-profit service organization. This non-profit service organization can act as an intermediate between the Medicare recipient and the pharmaceutical manufacturer that desires to help needy patients. In this regard, the non-profit service organization thus avoids any form of enticement or inducement issues that would be problematic by the direct donation by a pharmaceutical company of a drug product to address a patient's needs either by providing a drug product or to generate a value that may go toward true out-of-pocket expenses.

In one specific approach to providing needed product to a Part B recipient, the non-profit organization could seek drug product donations and replace the drug products as they are used in a hospital institution. More specifically, the non-profit organization can either approach pharmaceutical manufacturers to donate either drug product or cash in order to meet the needs of Medicare recipients under Part B or D, or pharmaceutical manufacturers knowing the existence of the non-profit organization may seek out the non-profit organization to provide donations thereto as shown in step 102 in FIG. 1. Once the drug product has been donated to the non-profit organization, the non-profit organization will then process the drug product through a financial eligibility process. More specifically, the non-profit organization will take "title" of the drug product. In this regard, the non-profit organization may not have physical possession of the product, but will take title of the product to allow easier transfer and distribution. The physical drug product may then be shipped to a pharmacy warehouse, non-profit pharmacy (that may be operated by the non-profit organization), contracted for profit pharmacy, or warehouse program where it is inventoried as shown in step 104.

Once it is determined that a patient needs a particular drug product, the physician can merely write a prescription for the drug product. Once the non-profit organization receives the request from the physician for the drug product to be used in a medical procedure, the non-profit organization can then process the prescription as is shown in step 108.

Finally, the drug product is used by the patient in a medical procedure. In this regard, the patient need not use the actual shipped and inventoried product as described above in step 104, the drug product may be used directly from the hospital's inventory. As shown in step 108, the non-profit organization will ship the drug product to the hospital to replace the drug product that was used by the Medicare patient or the Medicare patient may obtain the drug product from a non-profit pharmacy (that may be operated by the non-profit organization) or contracted for profit pharmacy. Accordingly, the non-profit organization thus provides for an ability to provide a drug product to a Medicare recipient without being entangled in any sort of enticements or inducement issues. One or more steps may be performed via a computer such as approaching drug companies and processing donations to meet requirements of taking title and the like.

Figure 2:
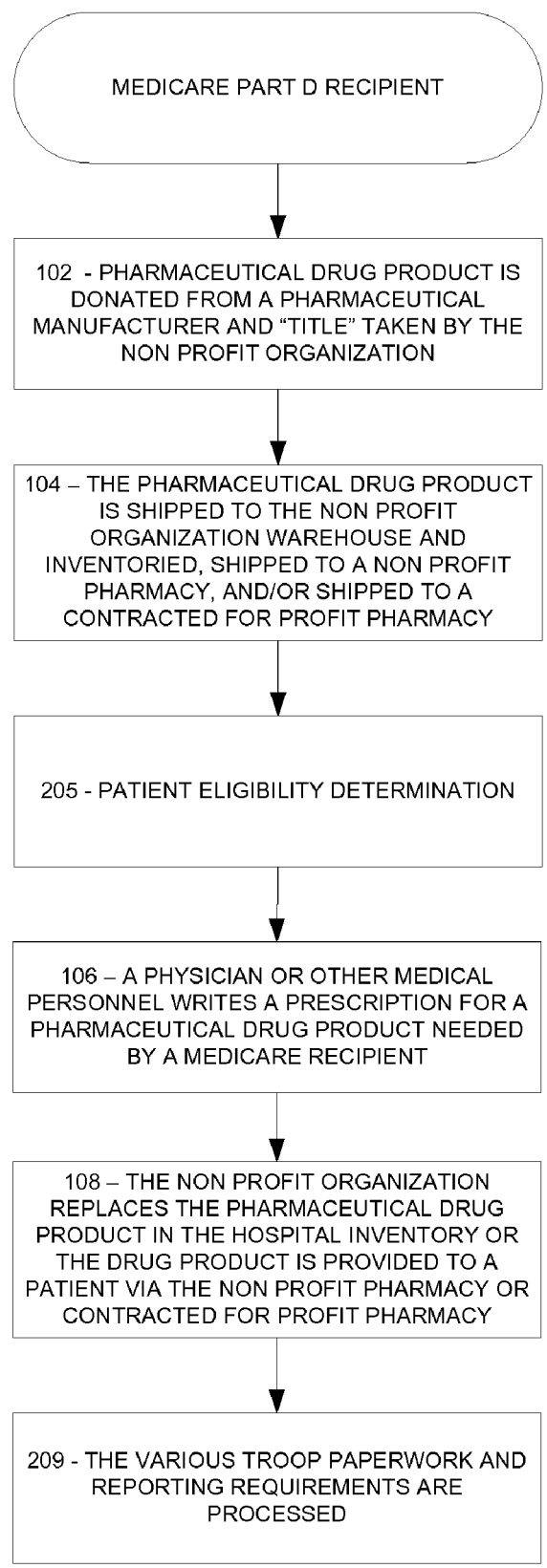
FIG. 2 illustrates a process flowchart for addressing the needs of Medicare Part D recipients according to the principles of the invention.

The process of addressing the needs of Medicare patients under Medicare Part D needing to satisfy the TrOOP expenses would be very similar to that of the above-described Part B recipient process. In particular, again a non-profit organization and/or non-profit pharmacy would be set up in order to avoid any enticement or inducement issues. As shown in FIG. 2, in step 102 the non-profit organization would receive drug donations from a pharmaceutical manufacturer and take a title thereto. Next, as shown in step 104 the drug product is shipped from the pharmaceutical manufacturer to the non-profit organization's pharmacy and inventoried.

The Part D approach includes the same steps as the Part B approach but differs in that it must now address various TrOOP issues. A Medicare Part D recipient may make an application and go through an eligibility process with the non-profit organization. This would allow the non-profit organization to make a financial determination whether a particular Medicare recipient should be entitled to TrOOP assistance. In this regard, it may be desired that patients with the most expensive chronic illnesses should be helped. Other criteria may also be used. By way of example, a computer processor may be used to accept and/or evaluate patient applications. Accordingly in step 205, the patients will go through an eligibility determination. In step 209 the various TrOOP paperwork and reporting requirements are processed. Accordingly, in step 209 the TrOOP processing and reporting requirements are completed and the donation of the drug product by the pharmaceutical manufacturer will count toward satisfying the TrOOP for the Medicare recipient. By way of example, the processing and reporting documentation may be completed using a personal computer, such as by completing documents and transmitting them over a network, such as the Internet. Because of the drug product donation arrangement with the non-profit organization, the pharmaceutical manufacturers will have a legal avenue to allow their free drug product to count toward TrOOP. On the other hand, the Medicare recipient will be allowed to receive life-saving or life-altering prescription medications. The Medicare recipients will thus have access to the prescriptions they need so that they may experience improved health without going financially bankrupt or becoming drug-resistant due to lack of continued access to the needed drugs.

In addition to providing life-saving product to patients, the pharmaceutical manufacturer also receives notable benefits to donating the free drug product. In the past, pharmaceutical manufacturers have engaged in various "patient assistance programs" that provided free drug product to needy patients. This free drug product never counted toward the patient's TrOOP. The free drug product could typically be written off as a marketing expense or could qualify as a cost-of-goods write-off. However, this write-off had very limited value. With a drug product donation by a pharmaceutical manufacturer to a non-profit organization, the donation has increased write-off value. In this regard, drug donations by a pharmaceutical manufacturer to a non-profit organization may qualify for a higher write-off such as, for example, twice the cost of goods. The increased write-off is a great incentive for pharmaceutical manufacturers to be philanthropic. It also allows the patient to satisfy his/her TrOOP in order to better afford treatment since the patient will now have a more affordable shared cost once this TrOOP has been satisfied.

Figure 3:
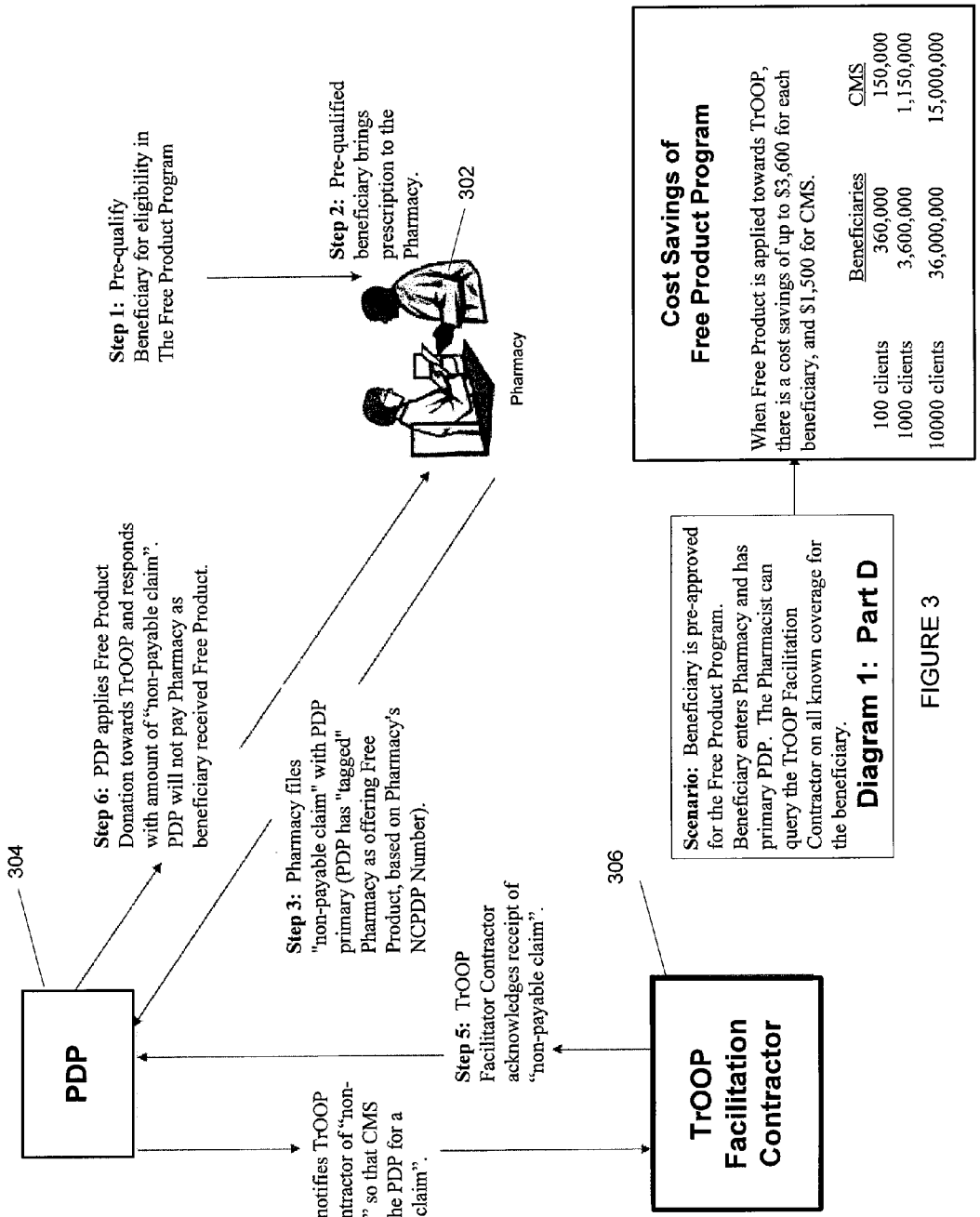
FIGS. 3 and 4 illustrate more detailed examples of implementation according to the principles of the invention.
Figure 4:
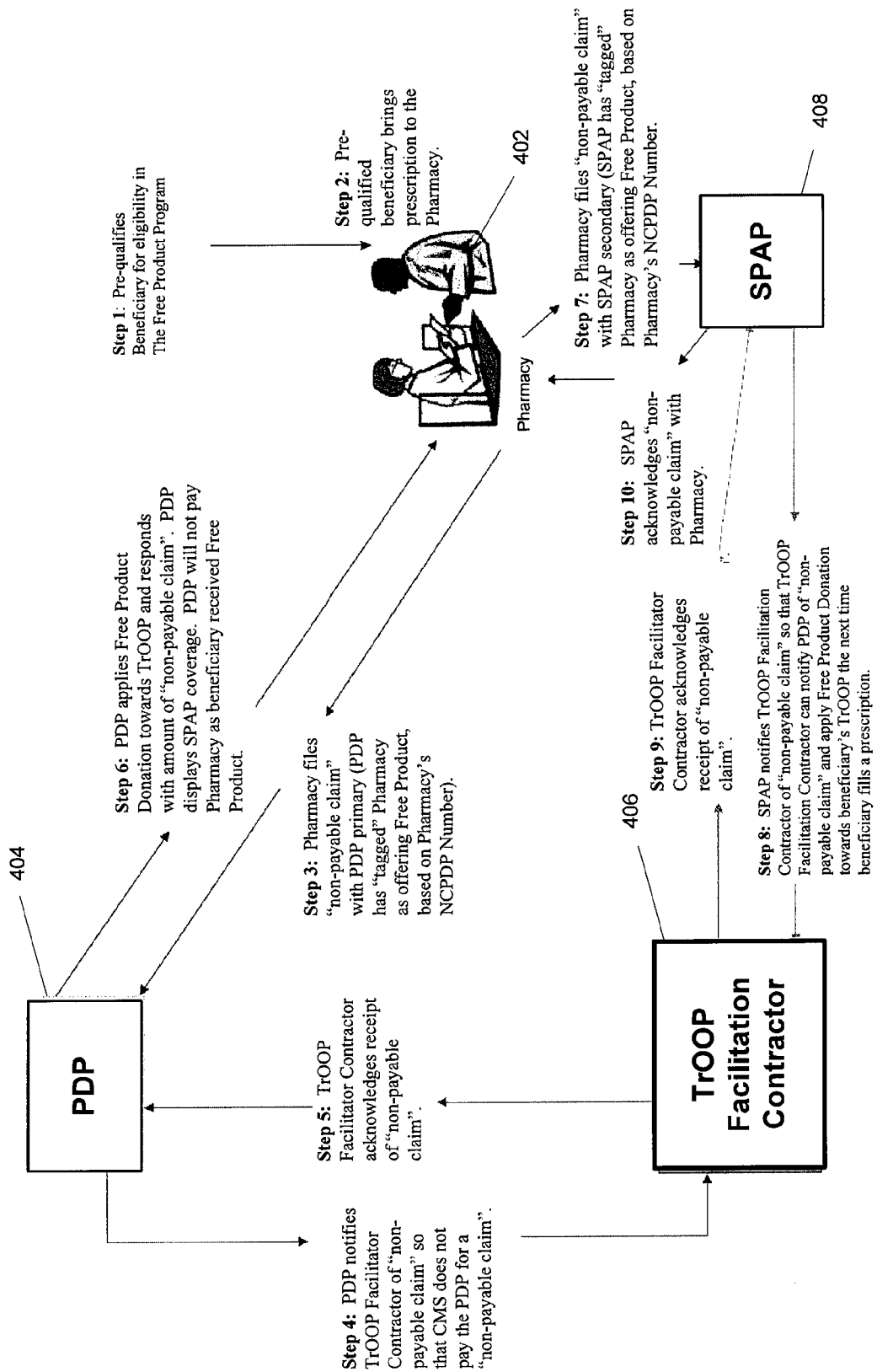

FIGS. 3 and 4 provide more specific detailed examples of two implementations of the invention for the two different scenarios.

In the first scenario shown in FIG. 3, the beneficiary is pre-approved for the Free Product Program. Beneficiary enters the pharmacy and has primary PDP. The Pharmacist can query the TrOOP Facilitation Contractor on all known coverage for the beneficiary.

Step 1: PSI pre-qualifies beneficiary for eligibility in the Free Product Program Step 2: Pre-qualified beneficiary brings prescription to the pharmacy at 302.

Step 3: Pharmacy 302 files a "non-payable claim" with a PDP primary 304 (PDP has "tagged" pharmacy as offering free product, based on pharmacy's NCPDP number). The filing may be performed over a network, such as the Internet.

Step 4: PDP 304 notifies a TrOOP Facilitator Contractor 306 of the "non-payable claim" so that the center for medical service ("CMS") does not pay the PDP 304 for a "non-payable claim".

Step 5: The TrOOP Facilitator Contractor 306 acknowledges receipt of "non-payable claim". The acknowledgement may occur by sending to the PDP, such as via the Internet or similar electronic transmission.

Step 6: The PDP 304 applies free product donation towards TrOOP and responds with amount of "non-payable claim." The PDP 304 will not pay the pharmacy 302 as a beneficiary of received free product.

In the second scenario shown in FIG. 2, the beneficiary is pre-approved for the free product program. Beneficiary enters pharmacy 402 and has primary PDP coverage and secondary state pharmacy assistance program ("SPAP") coverage. The Pharmacist can query the TrOOP Facilitation Contractor 406 on all known coverage for the beneficiary.

Step 1: A beneficiary is pre-qualified for eligibility in the free product program.

Step 2: A pre-qualified beneficiary brings prescription to the pharmacy 402.

Step 3: The Pharmacy 402 files "non-payable claim" with a PDP primary 404 (PDP has "tagged" Pharmacy as offering Free Product, based on Pharmacy's NCPDP Number). This filing may be performed electronically, such as by using a computer connected to a network such as the Internet.

Step 4: The PDP 404 notifies TrOOP Facilitator Contractor 406 of "non-payable claim" so that CMS does not pay the PDP for a "non-payable claim." This notification may be performed electronically, such as by using a computer connected to a network such as the Internet.

Step 5: The TrOOP Facilitator Contractor 406 acknowledges receipt of "non-payable claim." This acknowledgement may be transmitted electronically.

Step 6: The PDP 409 applies free product donation towards TrOOP and responds with amount of "non-payable claim." The PDP 404 displays SPAP coverage. The PDP will not pay the pharmacy 402 as the beneficiary received free product.

Step 7: The pharmacy 402 files a "non-payable claim" with a SPAP secondary 408 (SPAP has "tagged" Pharmacy as offering Free Product, based on Pharmacy's NCPDP Number. This filing may be done electronically, such as by using a computer connected to a network such as the Internet Step 8: The SPAP 408 notifies TrOOP Facilitation Contractor 406 of the "non-payable claim" so that the TrOOP Facilitation Contractor 406 can notify the PDP of "nonpayable claim" and apply the free product donation towards the beneficiary's TrOOP the next time the beneficiary fills a prescription. This notification may be done electronically, such as by using a computer connected to a network, such as the Internet.

Step 9: TrOOP Facilitator Contractor acknowledges receipt of "non-payable claim".

Step 10: The SPAP 408 acknowledges the "non-payable claim" with the pharmacy. Again, this acknowledgement may be performed electronically.

As noted above, when the pharmaceutical manufacturer makes a drug product donation to the non-profit organization, the drug product may be shipped from the designated pharmaceutical manufacturer to be inventoried and shipped as needed. However, in the event when a pharmacy is a "for-profit" pharmacy, it would need to establish a separate books and storage areas to avoid the donated drug products being confused for the regular non-donated or for-profit drug products. Moreover, once the drug product is requested, the for-profit pharmacy can only charge a reasonable fee for shipping, ancillaries, and recordkeeping (i.e., up to $150.00 depending upon the retail value of the drug).

Additionally, Medicare law allows only for a "dispensing fee," of approximately $5.00 to $6.00 per prescription for free drug product.

Additionally, another approach is to allow a non-profit pharmacy to exist under the non-profit organization. Accordingly, the non-profit pharmacy could then allow for the non-profit organization to provide funding for the program as requested.

While the invention has been described in terms of exemplary embodiments, those skilled in the art will recognize that the invention can be practiced with modifications in the spirit and scope of the appended claims. These examples given above are merely illustrative and are not meant to be an exhaustive list of all possible designs, embodiments, applications or modifications of the invention.

What is claimed is:

1. A process of providing recipients with financial help in addressing medical care comprising:
   receiving a pharmaceutical drug from a donor pharmaceutical manufacturer;
   inventorying the drug received from the pharmaceutical manufacturer;
   taking title of the drug from the pharmaceutical manufacturer;
   pre-qualifying by a computer processor a recipient for eligibility to receive donated drugs;
   determining an amount of allowable eligibility for the recipient based on a difference between an annual maximum true out-of-pocket (TrOOP) threshold and any previous true out-of-pocket payments made by the recipient including an amount of donated drug previously received by the recipient;
   dispensing the drug to the recipient based on said pre-qualifying step and the amount of eligibility;
   sending by the computer processor an automated message indicating an amount of a non-payable claim, wherein the amount of the non-payable claim includes a value of the drug to be credited toward the recipient's true out-of-pocket payment; and
   crediting the value of the drug toward the recipient's true out-of-pocket payment.

2. The process according to claim 1, wherein the recipient is a Medicare recipient.

3. The process according to claim 1, wherein the-drug is received, and dispensed by a non-profit pharmacy organization.

4. The process according to claim 1, wherein said step of pre-qualifying is based on the recipients previous coverage for the drug.

5. The process according to claim 4, wherein the previous coverage for the drug is Medicare coverage.

6. The process according to claim 1, wherein said step of pre-qualifying is based on the recipient's income.

7. The process according to claim 1, further comprising the step of halting the dispensing of the at least one drug when a predetermined amount of the drug has been dispensed.

8. The process according to claim 7, wherein the predetermined amount is based on the cost of the drug.

9. The process according to claim 7, wherein said step of halting is based on the recipient being eligible for coverage for the drug after receiving the predetermined amount.

10. A system for providing recipients with financial help in addressing medical care, the system comprising:
    a processor;
    a memory; and
    a communication device,
    wherein, the system is programmed with computer instructions that cause the processor to perform the steps of:
    inventorying drugs received from one or more pharmaceutical manufacturers;
    pre-qualifying a recipient for eligibility;
    determining an amount of allowable eligibility for the recipient based on a difference between an annual maximum true out-of-pocket (TrOOP) threshold and any previous true out-of-pocket payments made by the recipient including an amount of donated drug previously received by the recipient;
    dispensing at least one of the drugs to the recipient based on said pre-qualifying step and the amount of allowable eligibility; and
    sending an automated message regarding the dispensing of the at least one of the drugs including an indicator of an amount of a non-payable claim, wherein the amount of the non-payable claim includes a value of the at least one of the drugs to be credited toward the recipient's true out-of-pocket payment; and
    crediting the value of the at least one of the drugs toward the recipient's true out-of-pocket payment.

11. The system according to claim 10, wherein the recipient is a Medicare recipient.

12. The system according to claim 10, wherein the inventorying and dispensing are performed by a non-profit pharmacy organization.

13. The system according to claim 10, wherein the pre-qualifying is based on the recipient's previous coverage for the drugs.

14. The system according to claim 13, wherein the previous coverage for the drugs is Medicare coverage.

15. The system according to claim 10, wherein the pre-qualifying is based on the recipient's income.

16. The system according to claim 10, further comprising computer instructions that cause the processor to perform the step of halting the dispensing of the at least one of the drugs when a predetermined amount of the at least one of the drugs has been dispensed.

17. The system according to claim 16, wherein the predetermined amount is based on the cost of the at least one of the drugs.

18. The system according to claim 16, wherein the halting is based on the recipient being eligible for coverage for the at least one of the drugs after receiving the predetermined amount.

* * * * *